United States Patent [19]
Tada

[11] Patent Number: 5,804,389
[45] Date of Patent: Sep. 8, 1998

[54] METHOD FOR DETECTING ABNORMAL EPITHELIAL CELL SHEDDING

[75] Inventor: Masahiro Tada, Yamaguchi, Japan

[73] Assignee: Phanos Technologies, Inc., Beverly Hills, Calif.

[21] Appl. No.: 580,720

[22] Filed: Dec. 29, 1995

[51] Int. Cl.$^6$ .................. G01N 33/53; G01N 33/574; C07D 235/02; C07D 403/00
[52] U.S. Cl. .................. 435/7.1; 435/7.23; 435/4; 436/64; 436/172; 436/175; 436/800; 548/100; 548/302.7; 548/304.4; 424/9.6
[58] Field of Search .................. 435/4, 7.1, 7.23; 60/103, 160; 436/64, 800, 172, 175, 805; 548/100, 302.7, 304.4; 424/9.6

[56] References Cited

U.S. PATENT DOCUMENTS

| | | | |
|---|---|---|---|
| 4,622,298 | 11/1986 | Mansour et al. | |
| 4,751,188 | 6/1988 | Valet | 436/63 |
| 4,762,701 | 8/1988 | Horan et al. | 424/1.17 |
| 4,783,401 | 11/1988 | Horan et al. | 435/34 |
| 4,859,584 | 8/1989 | Horan et al. | 435/29 |
| 5,507,287 | 4/1996 | Palcic et al. | 128/633 |

FOREIGN PATENT DOCUMENTS

| | | |
|---|---|---|
| 0266194 | 5/1988 | European Pat. Off. |
| 0266195 | 5/1988 | European Pat. Off. |
| 0266196 | 5/1988 | European Pat. Off. |
| 0595506 | 5/1994 | European Pat. Off. |
| 3238353 | 4/1984 | Germany |
| 8910758 | 11/1989 | WIPO |
| 9526673 | 10/1995 | WIPO |

OTHER PUBLICATIONS

Eastwood, G.L., "Gastrointestinal epithelial renewal; implications for for mucosal protection and carcinogenesis", *Current Advances in Digestive Disease*, 1993, pp. 143–158.

Fox, et al., "A Tricarbocyanine Dye for Continuous Recording of Dilution Curves in Whole Blood Independent of Variations in Blood Oxygen Saturation", *Staff Meetings of the Mayo Clinic*, vol. 32, No. 18, Sep. 4, 1957, pp. 478–484.

Schad, et al., "Studies on the Suitability of a Cyanine Dye (Viher–Test®) for Indicator Dilution Technique and Its Application to the Measurement of Pulmonary Artery and Aortic Flow", *Pflügers Arch., European Journal of Physiology*, 370, 139–144 (1977).

Dow, P., "Estimations of Cardiac Output and Central Blood Volume by Dye Dilution", *Physiol. Rev.*, 36:77–102, Jan. 1956.

Sims, et al., "Studies on the Mechanism by Which Cyanine Dyes Measure Membrane Potential in Red Blood Cells and Phosphatidylcholine Vesicles", *Biochemistry*, vol. 13, No. 16, pp. 3315–3330 (1974).

Ida, et al., "Endoscopic Diagnosis of Gastric Cancer with Dye Scattering", *Am. J. of Gastroenterology*, pp. 316–320., 63/4, 1975.

Slezak, et al., "Fluorescent In Vivo Tracking of Hematopoietic Cells", *Blood*, vol. 74, No. 6 (Nov. 1), 1989, pp. 2172–2177.

Samlowski, et al., "Effects of Supravital fluorochromes used to analyze the in vivo homing of murine lymphocytes on cellular function", *Journal of Immunological Methods*, 144(1991) 101–115.

Hugo, et al., "A cell line that can induce thymocyte positive selection", *Nature*, vol. 360, Dec. 17, 1992, pp. 679–682.

Messina, et al., "Adhesion and incorporation of lacZ–transduced endothelial cells into the intact capillary wall in the rat", *Proc. Natl. Acad. Sci.*, vol. 89, pp. 12018–12022, Dec. 1922.

Melnicoff, et al., "In Vivo Labelling of Resident Peritoneal Macrophages", *Journal of Leukocyte Biology*, 43:387–397 (1988).

Melnicoff, et al., "Kinetics of Changes in Peritoneal Cell Populations following Acute Inflammation", *Cellular Immunology* 118:178–191 (1989).

Melnicoff, et al., "Maintenance of Peritoneal Macrophages in the Steady State", *Journal of Leukocyte Biology*, 44:367–375 (1988).

*Primary Examiner*—Ponnathapura Achutamurthy
*Assistant Examiner*—Padmashri Ponnaluri
*Attorney, Agent, or Firm*—Rothwell, Figg, Ernst & Kurz

[57] ABSTRACT

A method for detecting abnormal cell shedding rates of mature epithelial cells of a warm-blooded animal, such as the epithelial cells of the gastric or colonic glands. A labeling composition containing, e.g., a cyanine dye is applied to epithelial cells, following which the site is observed over time. Abnormal cell shedding rates are indicative of disease states such as carcinoma.

13 Claims, 1 Drawing Sheet

METHOD FOR DETECTING ABNORMAL EPITHELIAL CELL SHEDDING

FIELD OF THE INVENTION

The present invention relates to a method for detecting abnormal epithelial cell shedding rates in vivo, having utility as a diagnostic method.

DESCRIPTION OF THE RELATED ART

It is known that changes in epithelial cell kinetics (including the phenomena referred to as cell proliferation, migration, differentiation, senescence and loss) can be associated with different disease states, including inflammation and carcinomas (malignancies of epithelial cells). Thus, the establishment of accurate methods to measure cell kinetics is of great importance to the medical and related fields. Before the advent of autoradiography using tritiated thymidine (3H-thymidine), cell kinetics typically was determined using various methodologies including examining cell mitoses, measuring the size of gastric and intestinal glands (for example via microscopic counting or measuring), and by performing simple cell counting in in vitro cell cultures.

Conventional methods for the analysis of cell kinetics use markers associated with DNA synthesis in proliferating cells. Proliferating cells can be labeled with 3H-thymidine or the thymidine analogue, bromodeoxyuridine (BrdU), which are rapidly incorporated into cellular DNA during DNA synthesis. This method merely measures the rate of DNA synthesis, however, and does not directly measure cell growth, migration or shedding within the body.

Because of the relative ease of carrying out methods using markers associated with DNA synthesis, these methods generally have been the methods of choice for assessing epithelial cells suspected of exhibiting abnormal kinetics. The utility of these methods is limited by the fact that it is necessary to incubate 3H-thymidine and BrdU with proliferating cells for a fixed length of time. Moreover, labeling with 3H-thymidine and BrdU cannot be performed in vivo in humans. Human epithelial cell samples must be removed from the patient and subjected to tissue culture in a medium containing 3H-thymidine or BrdU.

Determining the levels of certain enzymes, such as proliferating cell nuclear antigen (PCNA) and thymidine kinase, also has been used to determine cell kinetics. While these methods do not require tissue culture, they have not been applied to an in vivo method for assessing cell kinetics, including cell migration or shedding.

Cyanine dyes have been used in various biological applications. Dioxacarbocyanine dyes have been used in performing white blood cell differential counts. Gunter Valet, Max Planck Ges Wissensch; Patent Accession Number 84-102307/17, *Simultaneous Quantitative Determination of Blood Cells by Selective Staining and Measuring Volume and Fluorescence.* The dyes utilized in these studies are short chain carbocyanine dyes (less than ten carbon atoms) and respond to changes in membrane potentials. The short chain carbocyanine dyes enter the cells' mitochondria, are cytotoxic, and, when the cells are washed, these dyes easily leak out of the cells whether or not the membrane potential of the cells is changed. Tricarbocyanine dyes (Fox, I. J., et al., *Proc. May Clinic,* 32: 478–484, 1957) and Evans-Blue dye (Schad, H., et al., *Pfluegers Arch. Eur. J. Physiol.,* 370(2): 139–144, 1977) have been used in vivo to estimate cardiac output by a dilution method. Dow (Dow, P., Physiol. Rev., 36: 77–102, 1956) describes the method as including the injection of a known amount of an intravascular indicator on the venus side of the lungs and measurement of the arterial concentration of the indicator over time to determine the volume between the points of injection and sampling. These dyes are not used to stain cells, however.

U.S. Pat. No. 4,762,701, the teachings of which are incorporated herein in their entirety, refers to in vivo methods for tracking cyanine labeled cells and for determining cell lifetimes by measuring the rate at which cyanine dye-labeled cells administered to a subject disappear.

U.S. Pat. No. 4,783,401, the teachings of which are incorporated herein in their entirety, refers to methods for labeling viable cells with cyanine dyes in order to, among other things, measure the growth rate of cultured cells.

U.S. Pat. No. 4,859,584, the teachings of which are also incorporated herein in their entirety, refers to methods for determining the growth rate of cyanine labeled cells growing in vitro and in vivo.

Prior to the instant invention cellular kinetics had not been studied by examining the shedding rate of mature surface epithelial cells in vivo. Therefore, the published literature contains very little data concerning shedding rates of healthy or abnormal mature epithelial cells found, for example, on the gastrointestinal or other mucosal surfaces. Cellular shedding in the stomach has been assessed by washing the stomach lining over a fixed length of time and measuring cell loss by measuring the presence of cellular DNA in the washing solution. This method has proven to be inaccurate because the procedures are complex and difficult to standardize, the cells acquired during washing may be inadequate for carrying out the DNA analysis, and cells from other than the designated target site may inadvertently be obtained during washing.

SUMMARY OF THE INVENTION

Accordingly, one object of the invention is to provide a method for detecting abnormal epithelial cell shedding rates in vivo.

Another object of the invention is to provide an in vivo method for diagnosing disease states which are characterized by the presence of abnormal cell shedding rates amongst mature epithelial cells by determining, in vivo, whether the shedding rate of surface epithelial cells at a target site of a warm-blooded animal is normal or abnormal.

Yet another object of the invention is to provide an improved method for diagnosing carcinomas, such as stomach and colon carcinomas, and other diseases that are characterized by abnormal epithelial cell shedding rates.

To achieve these and other objects, the present invention provides an in vivo method for detecting abnormal cell shedding rates amongst mature epithelial cells, such as epithelial cells of mucosal surfaces, of a warm-blooded animal comprising the steps of labeling mature surface epithelial cells at a target site and thereafter monitoring the site for the presence or absence of the label. In a preferred embodiment of this method, the cells which are labeled reside on mucosal surfaces, amongst which mucosal surfaces of the gastro-intestinal tract provide particularly preferred targets.

The present invention also provides a method for diagnosing disease states characterized by abnormal cell shedding rates amongst mature epithelial cells of a warm-blooded animal, comprising labeling mature epithelial cells, determining the shedding rate of the labeled cells and comparing the shedding rate of the labeled cells to the known shedding rate of similarly located healthy epithelial cells.

DESCRIPTION OF THE PREFERRED EMBODIMENTS

Figure 1:
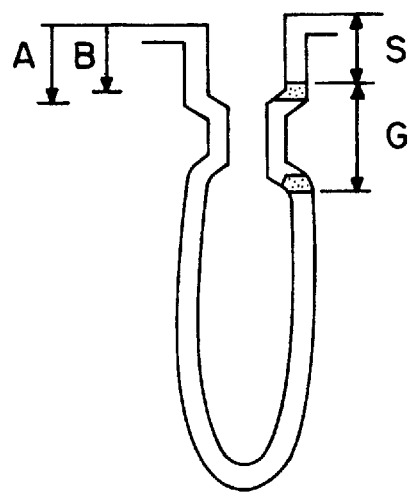
FIG. 1 is a schematic drawing of a portion of gastric mucosa.

Reference will now be made in detail to the presently preferred embodiments of the invention. The present invention provides an improved in vivo method for detecting abnormal cell shedding rates of mature epithelial cells of a warm-blooded animal, including humans. Mature, surface epithelial cells at a target site, for example a mucosal surface, are labeled with a labeling composition. A variety of labeling compositions suitable for labeling epithelial cells in vivo are known, including cyanine dyes, other chemical dyes such as crystal violate acetate, Hoechsdye H33342, Eosin and Floxyn, and antibody-based labels (e.g., a detectable moiety such as a fluorescent molecule, a radioactive isotope, a compound which is opaque to x-rays, etc., covalently linked to an antibody). Labeling compositions that contain a cyanine dye moiety are, presently, preferred. The cyanine dye moiety can function as the sole detectable specie in the labeling composition. Alternatively, an additional detectable specie such as another chemical dye, or a compound that is opaque to x-rays (i.e., an x-ray contrast agent) may be present in the labeling composition. The additional detectable specie may be chemcially coupled to the cyanine dye moiety, or may simply be present in admixture with the cyanine dye or other labeling compound.

The cell population that is targetted to be labeled in accordance with the present invention preferably consists predominantly, if not exclusively, of mature epithelial cells. Mature epithelial cells are those cells which, having completed mitosis, have lost the ability to proliferate. Thus, the loss of detectable label at the site is due to shedding (loss) of the labeled cells from the epithelium, as opposed to dilution of the label as a result of cell division amongst labeled cells.

The rate at which the labeled cells are shed from the site, as indicated by the loss of detectable label over a pre-defined period of time may be determined in a variety of manners. Direct visual observation of the site by the physician is presently preferred, although other means for determining the presence or absence of the label (for example, the use of x-ray or other radiological imaging in conjunction with an x-ray contrast agent label) can be employed.

The term 'abnormal cell shedding rates' as used herein means a greater (hyper-) or lesser (hypo-) than normal rate of cell shedding. The invention is unique in that the shedding rate of mature surface epithelial cells is directly assessed in vivo in order to assess cell kinetics and to aid in the determination of the presence of a disease state.

The integrity of tissue function and morphology cannot be maintained without cell renewal. The human gastric and colonic mucosa are examples of tissues that continuously undergo rapid cell loss (through intraluminal exfoliation and cell death) and renewal. In an organ where constant cell renewal occurs in order to maintain a certain number of cells, cell production and cell loss occur at approximately the same rate in healthy tissues. In gastric mucosa, gastric mucosal epithelial cells, which have a fixed life span, are generated in the proliferative zone located at the base of the pits and the contiguous upper portion of the glands. These cells migrate upward to the surface of the epithelium to replenish the mucous cells, differentiating and maturing in the process, and also downward to replace the cells of the gastric glands. Because gastric epithelial cells have advanced junction complexes, the order of the cells does not change during migration. As a result, older epithelial cells shed into the lumen first. This hierarchical shedding into the lumen, based upon cell age, is referred to as the "pipe line system." In the epithelium of the colon, the proliferative zone is located in the lower $\frac{2}{3}$ of the crypts. These cells also exhibit the "pipe line system" of hierarchical shedding but, unlike gastric epithelial cells, only migrate upwards. These processes, which are generally characterized by cell creation and cell loss in both healthy and abnormal epithelial tissues, are collectively referred to herein as "cell shedding."

It has now been discovered that when mature epithelial cells on the surface of, for example, a mucosal surface of an internal organ, are labeled, cell kinetics can be assessed by observing the rate at which the labeled cells are shed from the mucosal surface. The observed shedding rate can be compared to (1) the shedding rate of mature epithelial cells at another situs on the organ and/or (2) a standard shedding rate value for the particular type and location of cells that are being evaluated. Therefore, in contrast to the methodologies practiced to date to measure cell kinetics, the instant invention is practiced by measuring the shedding rate of differentiated, mature surface epithelial cells as opposed to measuring the growth rate of proliferating cells. Assessing the shedding rate of these mature surface epithelial cells gives the physician important information useful for the diagnosis and/or monitoring of the state of health of the epithelial cell population. Specifically, this information aids in the diagnosis and monitoring of hyper- and hypo-proliferation disorders and disease states characterized by abnormal cell kinetics, including carcinomas of the stomach and large intestine.

In order to detect an abnormal shedding rate of surface epithelial cells according to the instant invention, the cells are labeled with a detectable moiety which, in preferred embodiments, is a cyanine dye. The method is not limited to any particular target organ(s) or to any particular labeling composition, and is generally applicable to the study of cell shedding rates on any epithelialized surface (epithelium) of the body. Such surfaces include those of the stomach, biliary tract, colon, urinary tract, blood vessels, pulmonary tract including the nasal cavity, cornea, esophagus, pancreatic duct, small intestine, and genital organs including the vagina and ovarian duct and the prostate gland. The epithelialized linings of the stomach (the gastric mucosa) and the large intestine (the colonic mucosa) are the sites of carcinomas which are particularly common and are responsible for significant morbidity and mortality in large segments of the world's population. Accordingly, the invention has been illustrated in detail in connection with these two target sites.

In practicing the invention, the cell label should be selected such that its presence is readily identifiable when bound to a target epithelial surface. The label should attach to the epithelium without adversely changing the nature of the epithelial cells. The label should remain attached for sufficiently long periods of time and should be invulnerable to degradation for the period of time that the diagnostic procedure is carried out.

A preferred labeling composition for use in the method contains a cyanine dye of the formula:

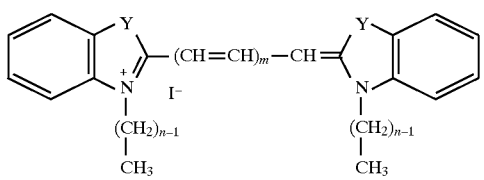

in which:

Y is oxygen, sulfur, methylene or alkyl-substituted methylene;

m is 0-3; and n can be the same or different and is 12-22.

As used herein, alkyl-substituted methylene refers to mono- or di-substituted methylene having any combination of methyl, ethyl, or propyl substituents. Compounds of the above structure are referred to by the generally understood shorthand formula:

$$DiYC_n \ (2m+1)$$

Sims, P. J., et al., *Biochem.*, 13:3315 (1974). Thus, for example, the compound wherein Y is sulfur and having three carbons bridging the rings and two fourteen carbon aliphatic chains is referred to as $DiSC_{14}(3)$. Similarly, $DiIC_{14}(5)$ indicates the compound wherein Y is isopropyl, and having five carbons bridging the rings and two fourteen carbon aliphatic chains.

Included within compounds referred to herein as cyanine dyes are compounds of the above structure having one or more substitutions, provided such substituted compounds are soluble in a cell labeling medium for at least as long as needed for labeling and have a sufficiently high membrane partition coefficient to remain associated with cell membranes. Such compounds also must not undesirably affect cell viability in the concentrations required for labeling. Also, pharmaceutically acceptable forms of the cyanine dye other than the iodide salt may be employed, including other pharmaceutically acceptable salts.

Most preferably, labeling is carried out with a composition comprising a cyanine dye of the formula

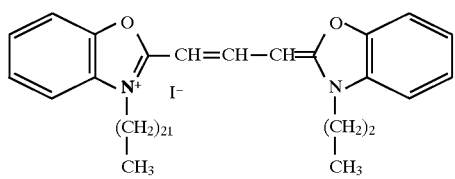

or

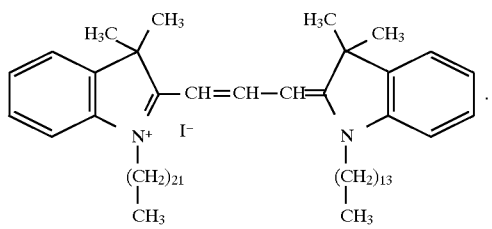

The dye of formula I, "PKH2" (1-docosanyl-1'-propyloxacarbanocyanine iodide) and the dye of formula II, "PKH26" (1-docosanyl-1'tetradecyl-3,3,3',3'-tetramethylindocarbanocyanine iodide) are commercially available from Sigma BioSciences and are manufactured by or for Phanos Technologies, Inc. Both PKH2 and PKH26 specifically and selectively stain cell membranes in vivo and do not undesirably affect the nature of the cells. Both dyes can be readily identified by the fluorescence they emit. These compounds also can act as binding agents with lipophilic affinity, to which other diagnostic compounds, or therapeutic compounds, can be attached.

In addition to these advantageous properties, PKH2 and PKH26 are non-antigenic, are not cytotoxic, have a long half-life, and have an ability to stain cells stably and consistently. The dyes need only be applied to surface epithelial cells for a few minutes to achieve adequate staining.

Other cyanine dyes can be purchased from various sources or can also be prepared from available starting materials using known synthetic methods. See Hamer, F. M., *The Cyanine Dyes and Related Compounds*, Interscience Publishers (1964). When in vivo use in humans is contemplated, a solution of PKH2 or PKH26 can be prepared by dissolving an effective amount of either dye in an aqueous sucrose solution. Both PKH2 and PKH26 are available in dye kits sold by Phanos Technologies, Inc. and which provide 500 μL of dye stock and 60 ml of diluent. Therefore, when preparing a dye solution using one of these kits the concentration of dye to diluent will be 1:120.

The concentration levels of PKH2 or PKH26 in compositions for use according to the present invention will be similar to the concentration levels used in the previously-known in vitro cell staining applications of those dyes. The precise concentration to be administered can be varied and can be readily optimized. The volume of dye composition to be administered will vary depending upon the concentration of the cyanine dye in the composition and upon the size of the target site. The administration volume may vary, for example, from about 1 to 100 ml, and an administration volume of about 10 ml of the dye composition can be used in many applications. The precise administration volume can be varied and can be readily optimized.

The labeling composition contains a cyanine dye in a medium (diluent) that is safe for administration and that provides reproducible cell labeling. Osmolarity regulating agents in which cyanine dyes form stable solutions for at least as long as required for labeling typically are used. Acceptable osmolarity regulating agents include sugars including monosaccharides such as glucose, fructose, sorbose, xylose, ribose, and disaccharides such as sucrose; sugar-alcohols including mannitol, glycerol, inositol, xylitol, and adonitol; amino acids including glycine and arginine; and certain Good's buffers such as N-tris (hydroxymethyl)-methyl-3-aminopropanesulfonic acid. Small amounts of buffering agents may be added to the labeling medium to regulate hydrogen ion concentration (pH). Other conventional agents, such as antibiotics and preservatives, may be employed.

In preparing the subject in order to practice the method of the present invention, the normal preparations required for carrying out an endoscopic examination are employed. Normal preparatory procedures such as fasting prior to the procedure should be followed. To increase the adhesion of cyanine dyes such as PKH2 and PKH26 to the epithelial mucosa, a mucus removing procedure utilizing a proteinase (PRONASE), manufactured by Kaken Seiyaku, may be employed. Such a mucus removing procedure is described in K. Ida et al., "Endoscopic Diagnosis of Gastric Cancer with Dye Scattering," *Amer. J. Gastroenterology*, Vol. 63, No. 4, pp. 316–320 (April 1975), the teachings of which are incorporated herein in their entirety. Briefly, antispasmodics are given 20 minutes prior to examination, followed by oral administration of about 80 ml of ten-fold diluted dimethylpolysiloxane (GASOON) solution mixed with 1 g of $NaHCO_3$ and 20,000 p.u. proteinase (PRONASE).

A variety of routes may be used to administer the labeling composition to the surface epithelial cells of the target site. The labeling composition may be administered using a delayed release oral dosage form. Preferably, the composition in solution form is administered by direct application (e.g. spraying) onto the surface of the epithelial mucosa under direct vision by endoscope, or by orally administering the solution to the subject in the form of a drink. While it is expected that directly spraying the solution onto the surface epithelium will provide superior adhesion to the mucosa, oral administration of the solution may be preferred due to the reduced burden on the subject.

According to one embodiment of the present invention, the labeling composition is applied to specific localized areas of epithelialized surfaces. A physician can readily ascertain upon endoscopic examination whether a localized area is likely to be abnormal and, thus, a good candidate for the shedding rate assessment procedure of the present invention. The physician may also apply the labeling composition to a neighboring, normal appearing site so as to provide a comparison between the two sites.

An advantage to applying the labeling composition to a localized area of cells as opposed to a substantial portion of the entire mucosal surface is the savings realized in dye material, and administration and diagnostic time. In preferred procedures, however, the labeling composition can be applied so as to cover a substantial portion of the entire mucosal surface of the internal target organ. When the cyanine dye is applied to a substantial portion of the entire stomach lining, for example, it is possible to observe abnormal shedding of mature endothelial cells by examining the fluorescence intensity at the site of the dyed epithelial cells.

When labeling gastric epithelial cells according to the invention, as opposed to epithelial cells of other organs, the length of time from administration of the labeling composition until observation is dependant on the fact that, on the average, the life span of gastric surface mucosal cells is about 2 days. Therefore, in assessing the shedding rate of gastric epithelial cells (wherein carcinoma results in slowing the normal shedding rate), at least one examination should be performed more than 2 days following administration. Conversely, in order determine whether a disease condition exists which has resulted in hyper-proliferation of cells in the gastric mucosa, at least one examination should be performed within the first 2 days following administration. During this time, the subject can maintain his or her normal lifestyle and diet with the exception that substances, such as aspirin and alcohol, that speed the shedding rate of gastric and other epithelial cells should be avoided.

The life span of the entire crypt in the colon is estimated to be about 4 to 7 days as observed in animal and human experiments. In general, four to seven days should pass after administration of the dye solution before an attempt to diagnose for colon cancer is made.

In practicing the invention, labeled surface epithelial cells may be directly visually observed. According to the preferred method of the invention, the shedding rate of such cells is assessed as being normal or abnormal by direct visual observation of labeled, mature epithelial cells present at, or absent from, the site of administration. Observable levels of fluorescence at the target site decrease as labeled cells are shed. The presence of label beyond the time in which normal epithelial cells at the labeled site would have been shed indicates hypoproliferation. Likewise, the disappearance of label prior to the time in which normal epithelial cells would have been shed indicates hyperproliferation. Advantageously, only a qualitative determination of the presence or absence of label can be made at a pre-selected time following the labeling procedure. While the amount of label can be quantitated, such is not necessary for carrying out the diagnostic procedure of the invention.

According to the preferred method of the invention, the cyanine dye label is detected by exposing the site of labeled cells to excitation light and observing and/or measuring the intensity of the fluorescence. For example, both PKH2 and PKH26 have a fixed absorption and fluorescent wavelength. PKH2 requires excitation light of about 490 nm to about 504 nm for the observation of maximum fluorescence, whereas PKH26 requires excitation light of about 551 nm to about 567 nm for the observation of maximum fluorescence. Fluorescence can be observed by an endoscopic instrument employing, for example, an appropriate filter and an optical detector.

In practicing the present invention, an ordinary fiberscope can be employed. Specifically, epithelial mucosa can be selectively exposed to light of specific wavelengths using a fiberscope with a filter that has been selected to transmit only a desired portion of the total spectrum. Preferably, the filter transmits light from a light source (such as a halogen lamp) having wavelengths of from about 490 nm to about 504 nm for PKH2 or from about 551 nm to about 567 nm for PKH26. Fluorescence is detected by passing light emitted from the labeled cells through an appropriate narrow band-pass filter, optionally through an image intensifier and to an optical detector which produces a signal corresponding to the intensity of the detected light. Other devices, such as an endoscope fitted with a high resolution CCD detector may be used for observing the site.

The available published data concerning shedding rates of mature epithelial cells from the gastrointestinal mucosa has been obtained via measurements of the volume of cell loss obtained by washing the stomach lumen, measuring DNA in the washing solution and measuring the number of detached cells in the gastric juice. According to this data, approximately 500,000 cells are shed from the gastric mucosa every minute. It is recognized that this cell loss increases during atrophic gastritis.

Although data on shedding rates has been limited, the cell kinetics of tumors is generally known. In general, when carcinoma develops in an organ in which the kinetics of healthy cell turnover is slow in healthy tissues, cell kinetics of the carcinoma cells increases. Conversely, if the cell kinetics of the epithelium of the healthy organ is high and carcinoma develops, the cell kinetics will decrease. Healthy liver cells, for example, undergo few cell divisions. Cell kinetics are increased in hepatic carcinoma cells. In healthy cells of the gastrointestinal mucosa, cell kinetics is normally extremely fast. Cell kinetics dramatically decreases when carcinoma is present.

The length of the S phase (the DNA synthesis phase) in the healthy human gastrointestinal mucosa is between about 10 to about 11 hours. It is known that the cycle time (T) in humans is from about 24 to about 48 hours for gastric mucosa, about 37 hours for intestinal metaplasia, about 40 hours for colonic mucosa, and from about 24 to about 48 hours for rectal mucosa. In comparison, the T in human stomach carcinoma is from about 2.5 to about 13 days and from about 4.2 to about 7.0 days for colon carcinoma. Therefore, it is clear that cell proliferation becomes noticeably slower in the presence of carcinoma. In addition, while the doubling time (D) for tumor cells (i.e., the time it takes for cell counts to double) in human carcinomas is typically in the range of from about 30 to about 120 days, it is extremely slow for gastrointestinal carcinoma; from about 555 to about 3,076 days for early stomach carcinoma, from about 105 to about 305 days for advanced stomach carcinoma, and approximately 636 days for colon carcinoma.

The difference in cell cycle times (T) among healthy and carcinoma cells is about ten-fold. This difference in growth rates will also be reflected in the epithelial shedding rates exhibited by normal and cancerous mucosal epithelial cells. The normal life span of gastric surface mucosal cells is from about 1 to 2 days. The normal life span of colonic mucosal epithelial cells is approximately 4 to 7 days. If the shedding rate of cancer cells were equal to this normal turnover, this would make the shedding rate of cancer cells faster than its T, which would essentially mean that cancer cells would disappear from the body. Therefore, it is believed that the shedding rate of cancer cells must be slower than the shedding rate of normal cells by a ten-fold difference (a difference similar to T of cancer cells and normal cells) in order for the cancer cells to remain in the body. Therefore, it is evident that there is a distinct difference in the shedding rates of normal and cancerous mucosa. The unique method of the present invention exploits this difference in shedding rates.

In practicing the invention, the precision of the particular instrument used to make the observation (i.e., to differentiate normal cells from carcinoma) is important. The two most commonly used endoscopes are the fiberscope and the electronic endoscope. While the resolution of fiberscopes and electronic endoscopes range widely among manufacturers, the fiberscope generally has a resolution of about 600$\mu$ and the electronic endoscope generally has a resolution of about 100$\mu$. As an objective of the invention, the shedding rate of epithelial cells within a lesion of from about 5 to about 10 mm in diameter should be distinguishable as normal or abnormal. Thus, an appropriate instrument should be chosen.

Since the shedding rate of normal gastric surface mucosal cells is about 2 days, significant disappearance of cyanine stain before that time is indicative of a condition in which the shedding rate is faster than normal. If the cyanine stain can be seen significantly beyond 2 days, this indicates that a condition exists (such as gastric carcinoma) whereby the shedding rate has slowed.

Atrophic gastritis generally progresses in the stomach mucosa with aging. Because cell turnover is known to increase during atrophic gastritis, it is believed that the shedding rate also increases.

Cell turnover in gastric ulcers is generally higher than in normal gastric tissues. There is no data on shedding rates, but to compensate for mucosal loss, normal growth takes place. Because of this, it is believed that cell loss is not delayed. It is also believed that there is a clear difference between this condition and gastric carcinoma, in which cell turnover is reduced.

The present invention is further described in the following examples which are provided for illustrative purposes only and are not to be construed as limiting.

EXAMPLE 1

In order to investigate whether cell kinetics can be analyzed by examination of shedding rates of labeled epithelial cells, PKH2 and PKH26 were used to stain epithelial cells in rat gastric mucosa. The objective of this study was to evaluate cell kinetics on the basis of migration and shedding rates of mature epithelial cells as opposed to the existing method of investigating DNA synthesis in proliferating cells. The following experiment was performed on 2 week old (160 to 200 g) male Wistar strain rats.

To decrease the residue in the stomach, the rats were fed a 7% sucrose, 0.5% NaCl solution for 2 days. To label the generative cell zone of the stomach mucosa, 50 mg/kg (about 10 mg per animal) of BrdU [5-bromo-2 deoxyuridine (Sigma Chemical Co.)] was given intraperitoneally 4 times at 6 hour intervals. Immediately after the fourth administration of BrdU, 3 ml of a pronase solution (pronase 20,000 units and 1 g sodium bicarbonate in 80 ml of water) was administered by an oral intubation tube for rats in order to remove surface mucus attached to the stomach mucosa. Thirty minutes after administering the pronase solution orally, 3 ml of PKH2 or PKH26 was administered to the stomach in the same way, using an oral intubation tube. At intervals of 1, 8, 16, 24, 32, 40, 48, 60, and 72 hours after the final BrdU administration, the rats were sacrificed and the stomach extracted and immediately frozen in liquid nitrogen.

The frozen tissues were cut by cryostat to make 4 serial sections of 5 $\mu$m thickness each.

The first frozen section was used to prove the existence of PKH2 or PKH26. This section was immediately mounted using a cyanoacrylic resin (BOND ARON ALPHA®, manufactured by Toa Gousei Kagaku Co.) to prepare a non-stained section. The remaining 3 frozen sections were fixed in 10% buffered formalin for 3 minutes. One section was stained with Hematoxylin-Eosin. The other 2 sections were stained by an enzyme-antibody method using an anti-BrdU monoclonal antibody as described below.

The sections were rinsed in 0.1M PBS (phosphate buffered saline, Experimental Bio Medical Research Inc.) and incubated in 2N HCl for 30 minutes at 37° C. to cleave DNA. The samples then were rinsed 3 times in 0.1M PBS. Then, to block the endogenous peroxidase, the samples were treated with 0.30%. $H_2O_2$ solution for 10 minutes at room temperature and washed 3 times in 0.1M PBS. Next, to block nonspecific reactions, the samples were incubated in double-diluted Block-ACE (Snow Brand Products Co. Ltd.) for 10 minutes and then washed 3 times in 0.1M PBS. Afterward, one section was incubated with a Primary Antibody (Anti-BrdU, Mouse monoclonal, Becton Dickinson) diluted 50 times by 0.1M PBS containing 1% BSA for 1 hour at room temperature. For negative control, the other section was incubated with normal mouse serum diluted 10,000 times in 0.1M PBS containing 1% BSA for 1 hour at room temperature. Afterward, the sections were rinsed 3 times with 0.1M PBS, followed by incubation with biotinylated mouse IgG for 30 minutes at room temperature. After rinsing 3 times with 0.1M PBS, the sections were reacted with ABC reagent (Vector) for 30 minutes at room temperature, again rinsed 3 times with 0.1M PBS, and then incubated in DAB solution (Dojindo) for 1 minute. After washing in running water, the sections were nuclear stained for 1 minute using Mayer Hematoxylin stain (Merck) and then washed again in running water for 10 minutes. The samples then were dehydrated with ethanol, cleared in xylene, and then embedded with HSR.

The following studies were conducted for the sections that were excised vertically to the mucosal surface. FIG. 1 shows various regions of a portion of excised gastric mucosa. The generative cell zone (G) is identified as the distance from the uppermost BrdU-stained cells to the lowermost BrdU-stained cells in the proliferative zone 1 hour after administering BrdU for the 4th time. The area above the uppermost BrdU-stained cells to the mucosal surface is called the surface mucosal cell zone (S). The ratio of BrdU-positive cells to the total number of cells in the generative cell zone at this point is called the proliferating zone labeling index.

Measurements were taken of the time it took for epithelial cells to migrate the distance from the BrdU-positive cells to the mucosal surface. The time elapsed for the BrdU-positive cells to reach the mucosal surface is called the renewal time of the surface mucosal cells. Also shown in FIG. 1 is the distance (A) which corresponds to the distance from the mucosal surface to the lowermost cells stained by PKH2 and the distance (B) which corresponds to the distance from the mucosal surface to the lowermost cells stained by PKH26.

The existence of PKH2 or PKH26 in the non-stained sections was examined using a fluorescent microscope. PKH2 was examined using a filter used for FITC and PKH26 was examined using a filter used for rhodamine. Measurements were taken of the distance from the mucosal surface stained with PKH2 and PKH26. The loss of stained cells is referred to as turnover. The histological measurements of the distances in each of the samples were measured using an objective micrometer.

The first hour after administering 50 mg/kg of BrdU for the fourth time in 6 hour intervals is considered the control specimen. BrdU-positive cells were predominately localized in the upper portion of the glands. Of the cells in the generative cell zone, 98.2% were BrdU-positive cells. Therefore, most of the cells in the generative cell zone had taken in BrdU.

The migration of surface mucosal cells was observed by successively examining the migration of BrdU-positive cells. In the first specimen, taken 1 hour after administration, the uppermost BrdU-positive cells could be seen at about $110\mu$ (i.e., a surface cell zone of $110\mu$ could be seen above the generative cell zone). Thus, it became clear that the BrdU-positive cells were migrating upward as time elapsed and at 60 hours after administration, BrdU-positive cells could be seen at the mucosal surface. Therefore, the life span of surface mucosal cells in rats was determined to be about 60 hours.

It has been reported that the life span of human surface mucosal cells is approximately 72 hours. The data obtained from the present studies pertaining to the time it took BrdU-labeled cells to reach the mucosal surface closely corresponds to that reported in the literature.

The dye PKH2 stained surface mucosal cells at a depth of about $75\mu$ from the mucosal surface. The depth of the PKH2 stain became more shallow as time elapsed and disappeared after 40 hours. PKH26 stained more shallow than PKH2, staining up to about $45\mu$ from the mucosal surface. The stained cell depth in this case also became more shallow as time elapsed, and the stain disappeared after 24 hours. The time it took for surface mucosal cells to shed was 60 hours as measured by BrdU at about $110\mu$, 40 hours for PKH2 stained at about $75\mu$ from the mucosal surface, and 24 hours for PKH26 stained at about $45\mu$. It is believed that the differences in shedding rates are a consequence of the differences in staining depths of each of the markers. As a result of this study, it is evident that PKH2 and PKH26 can be used as markers to analyze the shedding of surface mucosal cells.

EXAMPLE 2

In order to investigate whether cell kinetics can be analyzed by examination of shedding rates of labeled epithelial cells, PKH2 and PKH26 were used to stain epithelial cells in rat colonic mucosa. The following experiment was performed on 2 week old (160 to 200 g) male Wistar rats.

To decrease the residue in the colon, the rats were fed a 7% sucrose, 0.5% NaCl solution for 2 days. To label the generative cell zone of the colonic mucosa, 50 mg/kg (about 10 mg per animal) of BrdU was given intraperitoneally 4 times at 6 hour intervals. Immediately after the fourth administration of BrdU, 3 ml of a pronase solution (pronase 20,000 units and 1 g sodium bicarbonate in 80 ml of water) was administered through the anus in order to remove mucus attached to the colonic mucosa. Thirty minutes after administering the pronase solution, 3 ml of PKH2 or PKH26 was administered to the colon, also through the anus. At intervals of 1, 8, 16, 24, 32, 40, 48, 60, and 72 hours after administration, the rats were sacrificed and the colon was extracted and immediately frozen in liquid nitrogen.

The frozen tissues were cut by cryostat to make 4 serial sections of 5 $\mu$m thickness each.

The first frozen section was used to prove the existence of PKH2 or PKH26. This section was immediately mounted using a cyanoacrylic resin (BOND ARON ALPHA®, manufactured by Toa Gousei Kagaku Co.) to prepare a non-stained section. The remaining 3 frozen sections were fixed in 10% buffered formalin for 3 minutes. One section was stained with Hematoxylin-Eosin. The other 2 sections were stained by an enzyme-antibody method using an anti-BrdU monoclonal antibody as described below.

The sections were rinsed in 0.1M PBS (phosphate buffered saline, Experimental Bio Medical Research Inc.) and incubated in 2N HCl for 30 minutes at 37° C. to cleave DNA. The samples then were rinsed 3 times in 0.1M PBS. Then, to block the endogenous peroxidase, the samples were treated with 0.3% $H_2O_2$ solution for 10 minutes at room temperature and washed 3 times in 0.1M PBS. Next, to block nonspecific reactions, the samples were incubated in double-diluted Block-ACE (Snow Brand Products Co. Ltd.) for 10 minutes and then washed 3 times in 0.1M PBS. Afterward, one section was incubated with a Primary Antibody (Anti-BrdU, Mouse monoclonal, Becton Dickinson) diluted 50 times by 0.1M PBS containing 1% BSA for 1 hour at room temperature. For negative control, the other section was incubated with normal mouse serum diluted 10,000 times in 0.1M PBS containing 1% BSA for 1 hour at room temperature. Afterward, the sections were rinsed 3 times with 0.1M PBS, followed by incubation with biotinylated mouse IgG for 30 minutes at room temperature. After rinsing 3 times with 0.1M PBS, the sections were reacted with ABC reagent (Vector) for 30 minutes at room temperature, again rinsed 3 times with 0.1M PBS, and then incubated in DAB solution (Dojindo) for 1 minute. After washing in running water, the sections were nuclear stained for 1 minute using Mayer Hematoxylin stain (Merck) and then washed again in running water for 10 minutes. The samples then were dehydrated with ethanol, cleared in xylene, and then embedded with HSR.

Figure 2:
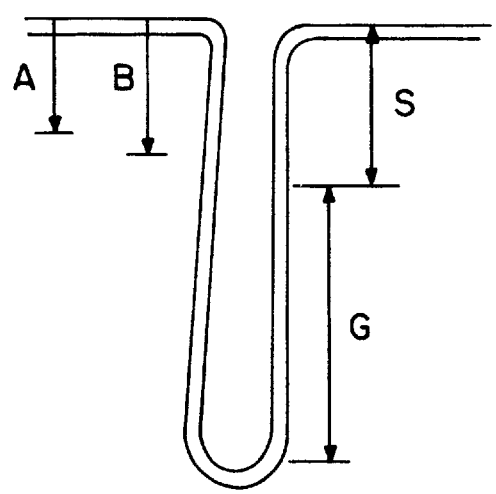
FIG. 2 is a schematic drawing of a portion of colonic mucosa.

The following studies were conducted for the sections that were excised vertically to the crypts. FIG. 2 shows various regions of a portion of excised colonic mucosa. The generative cell zone (G) is identified as the distance in the crypt from the uppermost BrdU-stained cells to the lowermost BrdU-stained cells in the proliferative zone 1 hour after administering BrdU for the 4th time. The area above the uppermost BrdU-stained cells to the mucosal surface is called the surface mucosal cell zone (S). The ratio of BrdU-positive cells to the total number of cells in the generative cell zone at this point is called the proliferating zone labeling index. Measurements were taken of the time it took for is epithelial cells to migrate the distance from the BrdU-positive cells to the mucosal surface. The time elapsed for the BrdU-positive cells to reach the mucosal surface is called the renewal time of the surface mucosal cells. Also shown in FIG. 2 is the distance (A) which corresponds to the distance from the mucosal surface to the lowermost cells stained by PKH2 and the distance (B) which corresponds to the distance from the mucosal surface to the lowermost cells stained by PKH26.

The existence of PKH2 or PKH26 in the non-stained sections was examined using a fluorescent microscope. PKH2 was examined using a filter used for FITC and PKH26 was examined using a filter used for rhodamine. Measurements were taken of the distance from the mucosal surface stained with PKH2 and PKH26. The loss of stained cells is referred to as turnover. The histological measurements of the distances in each of the samples were measured using an objective micrometer.

The first hour after administering 50 mg/kg (about 10 mg/animal) of BrdU for the fourth time in 6 hour intervals is considered the control period. BrdU-positive cells were predominately localized in the bottom $7/10$ths of the crypt. The upper $3/10$ths is the surface cell zone and measures about $60\mu$ in depth. of the cells in the generative cell zone, 98.2% were BrdU-positive cells. Therefore, most of the cells in the generative cell zone had taken in BrdU.

The migration of surface mucosal cells was observed by successively examining the migration of BrdU-positive cells. At one hour after administration, the highest BrdU-positive cells could be seen at about $60\mu$ (i.e., a surface cell zone of $60\mu$ could be seen above the generative cell zone). It became clear that the BrdU-positive cells were migrating upward as time elapsed and at 32 hours after administration, BrdU-positive cells could be seen at the mucosal surface. Therefore, the life span of surface mucosal cells in rats was determined to be about 32 hours. Because the life span in rats of BrdU-positive colonic surface mucosal cells, which occupied the upper $3/10$th of the crypt, was about 32 hours, the life span of the entire crypt is estimated to be about 107 hours or 4.5 days.

The life span of human surface mucosal cells has been reported to be approximately 4 to 7 days. The data obtained from the present studies pertaining to the time it took BrdU to reach the mucosal surface shows that the life span of colonic surface mucosal cells closely corresponds to the finding reported in the literature.

PKH2 stained surface mucosal cells at a depth of about $40\mu$ from the mucosal surface. The depth of the PKH2 label became more shallow as time elapsed, and in 16 hours the PKH2 label had disappeared. PKH26 stained deeper than PKH2, staining up to about $50\mu$ from the mucosal surface. The depth of this label also became more shallow as time elapsed, and had disappeared after 32 hours. The time it took for surface mucosal cells to shed was 32 hours as measured by BrdU at about $60\mu$, 16 hours for PKH2 stained at about $40\mu$, and 32 hours for PKH26 stained at about $50\mu$. It is believed that the differences in shedding rates are a consequence of the differences in staining depths of each of the markers.

EXAMPLE 3

In vivo examinations were performed in order to determine whether cancerous lesions could be differentiated from normal mucosa by identifying differences in shedding rates of cancerous human colonic and gastric cells as opposed to normal human colonic and gastric cells. The results obtained indicate that human colonic and gastric cancer can be diagnosed by measuring shedding rates.

PKH2- and PKH26-containing cell labeling compositions were sprayed upon target sites under direct vision by endoscopy, after which the diseased lesions as well as the normal mucosa surrounding the lesions were excised. Frozen sections were viewed under a fluorescent microscope to identify the presence of PKH2 or PKH26 and to measure shedding rates. In order to prepare the stomach for the procedure, gastric mucus was first eliminated using a solution containing pronase 20,000 units and 1 g sodium bicarbonate in 80 ml of water. Subsequent to this cleaning, a normal colonoscopic examination was performed in which PKH2 or PKH26 solution was sprayed under direct vision by endoscope to the lesion and surrounding area.

In the colon, a colonoscopic examination was performed and the diseased areas excised after normal colonoscopy preparations using approximately 137 g of polyethylene glycol plus two to four liters of water were performed. Prior to the follow-up examination, which was performed four days after the initial examination, the patient refrained from ingesting food, drugs, and other agents such as steroids, aspirin, and alcohol that have the potential to affect cell kinetics.

Because the cases studied involved early stage carcinoma, an endoscopic resection (a strip biopsy) was performed to excise the lesions. The excised sections were immediately preserved in liquid nitrogen. Two sections were created by slicing the tissue into 5 $\mu$m sections using a cryostat. After preparation of the frozen sections, one of the sections was immediately mounted and a non-stained preparation was created in order to identify the presence of PKH2 or PKH26. The second section was fixed in 10% buffered formalin for 3 minutes and then stained with Hematoxylin-Eosin. The diagnosis of the lesion was performed on the Hematoxylin-Eosin stained section. A fluorescent microscope and a filter used for FITC were used to identify the presence of PKH2 and a fluorescent microscope and a filter used for rhodamine were used to identify the presence of PKH26.

Patient 1

Patient 1 was a 60 year old male with early gastric carcinoma (elevated type, type IIa) in the antrum, 20 mm in diameter. After performing the mucus removing procedure using pronase 20,000 units and 1 g sodium bicarbonate in 80 ml water, a normal endoscopic examination was performed. Upon visually confirming the presence of lesions using an endoscope, 10 ml of a PKH2 solution was sprayed in order to stain the lesions. Four days after the endoscopic examination, the type IIa early gastric carcinoma was excised using a strip biopsy procedure. The tissue sections were frozen using the method described above and were examined under the microscope. From the image of the H-E stained tissue, it was evident that the region of well differentiated adenocarcinoma was localized in the mucosa with normal mucosa around it. Based on observation of cancerous regions with a fluorescent microscope using a FITC filter, it was revealed that the surface of the cancerous tissues was stained with PKH2 up to a depth of $30\mu$.

In contrast, while intestinal metaplasia and pyloric glands were recognized in the surrounding normal cells, PKH2 fluorescence was not detected. Thus, normal mucosal epithelial cells stained by PKH2 were lost due to shedding, while cancer cells stained by PKH2 were not.

Patient 2

Patient 2 was a 63 year old male with rectal carcinoma (elevated type I rectal carcinoma), 10 mm in diameter. A colonoscopy was performed after clearing the duct with polyethylene glycol. Upon visually confirming the presence of lesions using an endoscope, 10 ml of a PKH26 solution was sprayed onto the lesions and surrounding area. Four days later a colonoscopy was performed and the lesions were excised under direct vision by endoscope. The excised tissues were prepared using the same procedure as heretofore described in reference to patient 1. The H-E stained tissue showed well differentiated adenocarcinoma localized on the mucosa, and inspection by a fluorescent microscope revealed that the surface of the cancerous tissues was stained with PKH26 up to a depth of 60μ. It was also revealed that the epithelial cells stained with PKH26 in the surrounding mucosa were shed. Therefore, normal mucosa stained with PKH26 was shed while cancerous mucosa stained with PKH26 remained. Thus, it is evident that there are differences in shedding rates between cancerous and normal colonic mucosa.

In colonic mucosa, the zone of proliferating cells comprises the basal two thirds of the crypts. When measurements were carried out in vivo, the S phase duration was between 9 and 20 hours, and the total cycle time was between 24–48 hours. The population of cells in S phase for the large intestine (or labeling index (L.I.)) according to in vivo experiments varied between 12–25%. The replacement time for this tissue as calculated from these values is in the order of 4 to 8 days. In vitro studies generally provide shorter S phase durations (7.2–11.2 hours) and lower values of labeling indices (1.5–17%). Consequently, estimates for the total cell time have provided longer values than those obtained in vivo (77.2–129.9 hours in vitro vs. 24–48 hours in vivo).

The above description and drawings are only illustrative of a preferred embodiment which achieves the objects, features, and advantages of the present invention, and it is not intended that the present invention be limited thereto. Any modifications of the present invention which come within the spirit and scope of the following claims is considered part of the present invention.

I claim:

1. A method for assessing the shedding rate of mature surface epithelial cells on a mucosal surface of the gastrointestinal tract of a warm-blooded animal, comprising applying to mature surface epithelial cells at a target site a labeling composition comprising a dye, and determining the rate at which the dye is lost from the target site.

2. A method according to claim 1 wherein the dye is of the formula

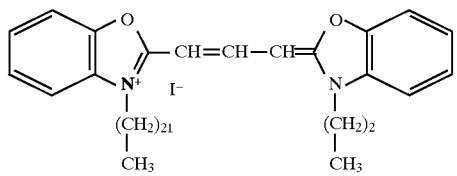

or

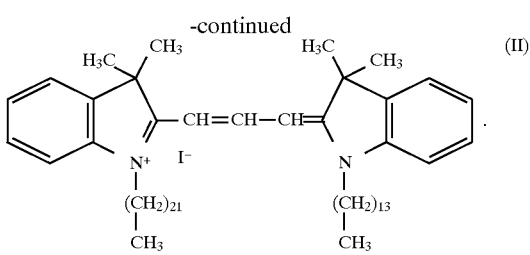

3. The method of claim 1 wherein the target site is a mucosal surface of the stomach.

4. The method of claim 1 wherein the target site is a mucosal surface of the colon.

5. The method of claim 1 wherein cell shedding rate is determined by observing changes in the level of the dye at the target site at a pre-selected time following said applying step.

6. The method of claim 5 wherein the dye is a cyanine dye and changes in the level of the dye are observed by exposing the target site to excitation light and detecting the intensity of fluorescence resulting therefrom.

7. The method of claim 6 wherein the excitation light has a wavelength of from about 490 nm to about 504 nm or from about 551 nm to about 567 nm.

8. The method of claim 1 wherein the epithelial cells are labeled by direct application of a labeling composition to the target site.

9. A method according to claim 1 wherein the epithelial cells are labeled by orally administering a labeling composition to the warm-blooded animal.

10. A method according to claim 1 wherein the epithelial cells are labeled by rectally administering a labeling composition to the warm-blooded animal.

11. A method according to claim 1 comprising removing mucous from the target site prior to applying a labelling composition.

12. A method according to claim 1 wherein the dye is a cyanine dye.

13. A method according to claim 12 wherein the cyanine dye is of the formula:

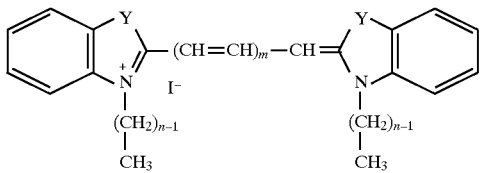

in which:

Y is oxygen, sulfur, methylene or alkyl-substituted methylene;

m is 0-3; and n is the same or different and is 12-22.

* * * * *